United States Patent [19]

Takaya et al.

[11] Patent Number: 4,464,369

[45] Date of Patent: * Aug. 7, 1984

[54] 7-ACYLAMINO-3-CEPHEM-4-CARBOXYLIC ACID DERIVATIVES AND PHARMACEUTICAL COMPOSITIONS

[75] Inventors: Takao Takaya, Kawanishi; Hisashi Takasugi, Osaka; Kiyoshi Tsuji; Toshiyuki Chiba, both of Osaka, all of Japan

[73] Assignee: Fujisawa Pharmaceutical Co., Ltd., Osaka, Japan

[*] Notice: The portion of the term of this patent subsequent to Aug. 16, 2000 has been disclaimed.

[21] Appl. No.: 355,339

[22] Filed: Mar. 8, 1982

Related U.S. Application Data

[60] Continuation-in-part of Ser. No. 886,340, Mar. 14, 1978, Pat. No. 4,425,341, and a continuation-in-part of Ser. No. 302,613, Sep. 15, 1981, Pat. No. 4,399,133, which is a division of Ser. No. 886,340.

[30] Foreign Application Priority Data

Mar. 14, 1977 [GB] United Kingdom ............... 10699/77
Jul. 12, 1977 [GB] United Kingdom ............... 29245/77
Oct. 11, 1977 [GB] United Kingdom ............... 42315/77
Jan. 3, 1978 [GB] United Kingdom ...................... 75/78

[51] Int. Cl.³ .................. A61K 31/545; C07D 501/22
[52] U.S. Cl. ....................................... 424/246; 544/22
[58] Field of Search ........................... 544/22; 424/246

[56] References Cited

U.S. PATENT DOCUMENTS 3,971,778  7/1976  Cook et al. ............................ 544/27
4,399,133  8/1983  Takaya et al. ........................ 544/22

Primary Examiner—Paul M. Coughlan, Jr.
Attorney, Agent, or Firm—Oblon, Fisher, Spivak, McClelland & Maier

[57] ABSTRACT

A compound of the formula:

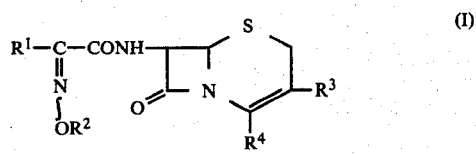

in which
$R^1$ is thiadiazolyl,
$R^2$ is carboxy(lower)alkyl or protected carboxy(lower)alkyl,
$R^3$ is hydrogen, halogen or lower alkenyl, and
$R^4$ is carboxy or a protected carboxy group, and pharmaceutically acceptable salts thereof, processes for making them, pharmaceutical compositions containing them and their use in treating infectious diseases.

19 Claims, No Drawings

7-ACYLAMINO-3-CEPHEM-4-CARBOXYLIC ACID DERIVATIVES AND PHARMACEUTICAL COMPOSITIONS

This application is a continuation-in-part of application Ser. No. 886,340 filed Mar. 14, 1978, now U.S. Pat. No. 4,425,341, and of application Ser. No. 302,613 filed Sept. 15, 1981, now U.S. Pat. No. 4,399,133, which is a division of said application Ser. No. 886,340.

The present invention relates to novel 7-acylamino-3-cephem-4-carboxylic acid derivatives and pharmaceutically acceptable salts thereof.

More particularly, it relates to novel 7-acylamino-3-cephem-4-carboxylic acid derivatives and pharmaceutically acceptable salts thereof, which have antimicrobial activity, to processes for the preparation of the same, to a pharmaceutical composition comprising the same, and to a method of using the same therapeutically in the treatment of infectious diseases in human being or animals.

Accordingly, one object of the present invention is to provide novel 7-acylamino-3-cephem-4-carboxylic acid derivatives and pharmaceutically acceptable salts thereof, which are highly active against a number of pathogenic microorganisms and are useful as antimicrobial agents, especially for oral administration.

Another object of the present invention is to provide processes for the preparation of novel 7-acylamino-3-cephem-4-carboxylic acid derivatives and salts thereof.

A further object of the present invention is to provide a pharmaceutical composition comprising, as active ingredients, said 7-acylamino-3-cephem-4-carboxylic acid derivatives and pharmaceutically acceptable salts thereof.

Still further object of the present invention is to provide a method of using said 7-acylamino-3-cephem-4-carboxylic acid derivatives and pharmaceutically acceptable salts thereof in the treatment of infectious diseases by pathogenic microorganisms in human being or animals.

The object 7-acylamino-3-cephem-4-carboxylic acid derivatives are novel and can be represented by the following general formula:

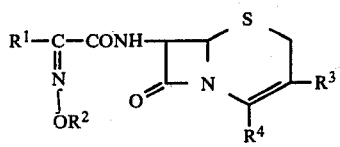

in which
$R^1$ is thiadiazolyl,
$R^2$ is carboxy(lower)alkyl or protected carboxy(lower)alkyl,
$R^3$ is hydrogen, halogen or lower alkenyl, and
$R^4$ is carboxy or a protected carboxy group.

In the object compounds (I) and the starting compounds (II) and (III) mentioned below, it is to be understood that there may be one or more stereoisomeric pair(s) such as optical and/or geometrical isomers due to asymmetric carbon atom and double bond in those molecules and such isomers are also included within the scope of the present invention.

With regard to geometrical isomers in the object compounds (I) and the starting compounds (III), it is to be noted that, for example, the object compounds (I) include syn isomer, anti isomer and a mixture thereof, and the syn isomer means one geometrical isomer having the partial structure represented by the following formula:

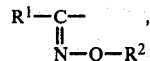

wherein $R^1$ and $R^2$ are each as defined above, and the anti isomer means the other geometrical isomer having the partial structure represented by the following formula:

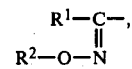

wherein $R^1$ and $R^2$ are each as defined above.

Suitable pharmaceutically acceptable salts of the object compounds (I) are conventional non-toxic salts and may include a salt with a base such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), and the like.

According to the present invention, the object compounds (I) and the pharmaceutically acceptable salts thereof can be prepared by the processes as illustrated by the following reaction schemes.

(1) Process 1:

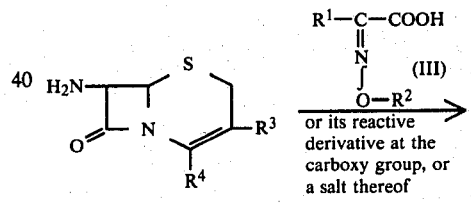

(II)
or its reactive
derivative at
the amino group,
or a salt thereof

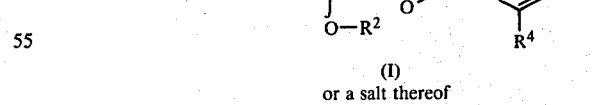

(I)
or a salt thereof (2) Process 2:

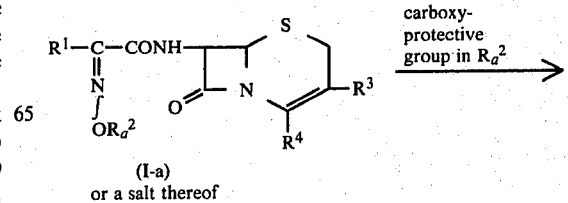

(I-a)
or a salt thereof

-continued

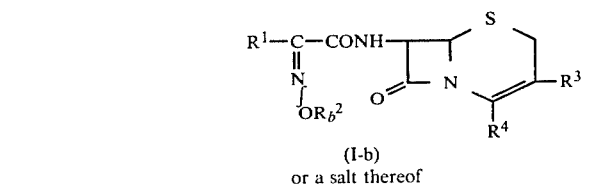

(I-b)
or a salt thereof (3) Process 3:

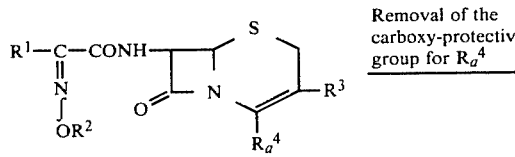

(I-C)
or a salt thereof

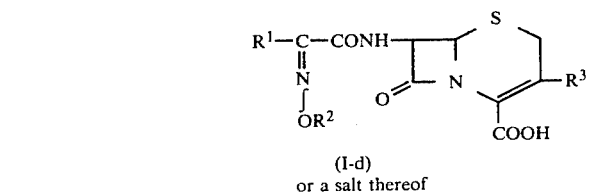

(I-d)
or a salt thereof in which
R$^1$, R$^2$, R$^3$ and R$^4$ are each as defined above,
R$_a^2$ is protected carboxy(lower)alkyl,
R$_b^2$ is carboxy(lower)alkyl, and
R$_a^4$ is a protected carboxy group.

Some of the starting compounds (III) used in Process 1 are new and can be prepared, for example, by the following methods.

Method A:

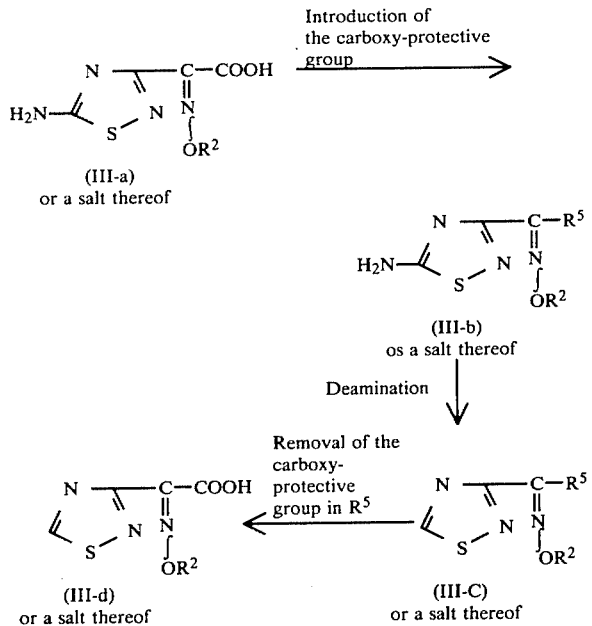

in which
R$^5$ is a protected carboxy group and
R$^2$ is as defined above.

Method B:

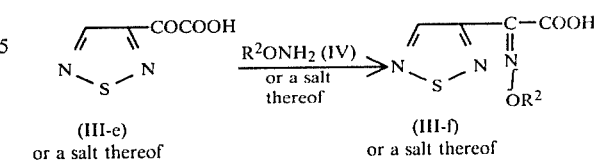

in which R$^2$ is as defined above.

In the above and subsequent description of the present specification, suitable examples and illustration of the various definitions to be included within the scope thereof are explained in details as follows.

The term "lower" in the present specification is intended to mean a group having 1 to 6 carbon atoms, unless otherwise indicated.

Suitable "thiadiazolyl" group may include 1,2,4-thiadiazolyl (i.e. 1,2,4-thiadiazol-3-yl and 1,2,4-thiadiazol-5-yl), 1,2,5-thiadiazolyl (i.e. 1,2,5-thiadiazol-3-yl), and the like, in which the preferred one is 1,2,4-thiadiazolyl and the most preferred one is 1,2,4-thiadiazol-3-yl.

Suitable "lower alkyl" moieties of the "carboxy(lower)alkyl" and "protected carboxy(lower)alkyl" groups may include straight or branched one such as methyl, ethyl, propyl, isopropyl, butyl, isobutyl, pentyl, isopentyl, neopentyl, hexyl and the like, in which the preferred one is C$_1$–C$_4$ alkyl, and the most preferred one is methyl.

Suitable "protected carboxy group" and "protected carboxy" moiety in the "protected carboxy(lower)alkyl" group may include an esterified carboxy group which is conventionally used in penicilin or cephalosporin compounds at their 3rd or 4th position thereof.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), mono- or di- or trihalo(lower)alkyl ester (e.g. chloromethyl ester, bromomethyl ester, 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 1-acetoxyethyl ester, 1-propionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s)) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), lower alkyl-substituted-2-oxo-1,3-dioxolyl (e.g. 5-methyl-2-oxo-1,3-dioxol-4-yl, etc.), and the like.

Preferred examples of "carboxy(lower)alkyl" for $R^2$ and $R_b^2$ thus defined may include carboxymethyl, 1-carboxyethyl, 2-carboxyethyl, 1-carboxypropyl, 3-carboxypropyl, 1-carboxy-1-methylethyl, 4-carboxybutyl, 5-carboxypentyl, 6-carboxyhexyl, and the like, in which the more preferred one is carboxy($C_1$–$C_4$)alkyl, and the most preferred one is carboxymethyl.

Preferred examples of "protected carboxy(lower)alkyl" for $R^2$ and $R_a^2$ thus defined may include lower alkoxycarbonyl(lower)alkyl (e.g. methoxycarbonylmethyl, ethoxycarbonylmethyl, propoxycarbonylmethyl, tert-butoxycarbonylmethyl, pentyloxycarbonylmethyl, 1-tert-butoxycarbonylethyl, 2-tert-butoxycarbonylethyl, 1-tert-butoxycarbonylpropyl, 3-tert-butoxycarbonylpropyl, 1-tert-butoxycarbonyl-1-methylethyl, 4-tert-butoxycarbonylbutyl, 5-tert-butoxycarbonylpentyl, 6-tert-butoxycarbonylhexyl, etc.), ar(lower)alkoxycarbonyl(lower)alkyl which may have nitro such as mono- or di- or triphenyl(lower)alkoxycarbonyl(lower)alkyl which may have nitro (e.g. benzyloxycarbonylmethyl, p-nitrobenzyloxycarbonylmethyl, benzhydryloxycarbonylmethyl, trityloxycarbonylmethyl, 1-benzhydryloxycarbonylethyl, 3-benzhydryloxycarbonylpropyl, 4-benzyloxycarbonylbutyl, 4-nitrobenzyloxycarbonylpentyl, benzhydryloxycarbonylhexyl, etc.), in which the more preferred one is $C_1$–$C_5$ alkoxycarbonyl($C_1$–$C_3$)alkyl, and the most preferred one is tert-butoxycarbonylmethyl.

Preferred examples of "a protected carboxy group" for $R^4$ and $R_a^4$ thus defined may include ar(lower)alkoxycarbonyl which may have nitro such as mono- or di- or triphenyl(lower)alkoxycarbonyl which may have nitro (e.g. benzyloxycarbonyl, p-nitrobenzyloxycarbonyl, benzhydryloxycarbonyl, trityloxycarbonyl, phenethyloxycarbonyl, phenylpropoxycarbonyl, phenylbutoxycarbonyl, phenylhexyloxycarbonyl, etc.), and the like, in which the more preferred one is mono- or di- or triphenyl($C_1$–$C_3$)alkoxycarbonyl which may have nitro, and the most preferred one is benzhydryloxycarbonyl and p-nitrobenzyloxycarbonyl.

Suitable "halogen" may include fluoro, chloro, bromo, or iodo, in which the preferred one is chloro.

Suitable "lower alkenyl" group may include straight or branched one such as vinyl, 1-propenyl, allyl 1-(or 2- or 3-)butenyl, 1-(or 2- or 3- or 4-)pentenyl, 1-(or 2- or 3- or 4- or 5-)hexenyl, 2-methyl-2-propenyl, and the like, in which the preferred one is $C_2$–$C_5$ alkenyl, and the most preferred one is vinyl.

Particularly, the preferred embodiment of the term $R^1$ is 1,2,4-thiadiazolyl and 1,2,5-thiadiazolyl; that of the term $R^2$ is carboxy(lower)alkyl; that of the term $R^3$ is hydrogen, halogen and lower alkenyl; and that of the term $R^4$ is carboxy.

The processes for preparing the object compounds (I) of the present invention are explained in details in the following.

(1) Process 1:

The compound (I) or a salt thereof can be prepared by reacting the compound (II) or its reactive derivative at the amino group, or a salt thereof with the compound (III) or its reactive derivative at the carboxy group, or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silylating agent such as bis(trimethylsilyl)acetamide, trimethylsilylacetamide, bis(trimethylsilyl)urea, or the like; and the like.

Suitable salt of the compound (II) may include the same one as those given for the object compounds (I), and further an acid addition salt such as an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. aspartic acid, glutamic acid, etc.), and the like.

Suitable reactive derivative at the carboxy group of the compound (III) may include an acid halide, an acid anhydride, an activated amide, an activated ester, and the like. The suitable example may also be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, thiazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hyroxysuccinimide, N-hydroxyphthalimide, 1-hydroxy-6-chloro-1H-benzotriazole, etc.), and the like, and these reactive derivatives can optionally be selected from them according to the kind of the compound (III) to be used.

Suitable salt of the compound (III) may include the same one as that given for the object compounds (I).

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction, or a mixture thereof.

When the compound (III) is used in a free acid form or its salt form in this reaction, the reaction is preferably carried out in the presence of a conventional condensing agent such as carbodiimide compounds (e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide,); N,N'-carbonyl-bis-(2-methylimidazole); keteneimine compounds (e.g. pentamethyleneketene-N-cyclohexylimine, diphenylketene-N-cyclohexylimine,); ethoxyacetylene; 1-alkoxy-1-chloroethylene; trialkyl phosphite (e.g. trimethyl phosphite); ethyl polyphosphate; isopropyl polyphosphate;

phosphorus oxychloride; phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, etc.), pyridine, N-lower alkylmorphorine (e.g. N-methylmorphorine, etc.), N,N-di(lower)alkylbenzylamine (e.g. N,N-dimethylbenzylamine, etc.), and the like.

The reaction temperature is not critical, and the reaction is usually carried out under from cooling to warming.

(2) Process 2:

The compond (I-b) or a salt thereof can be prepared by subjecting the compound (I-a) or a salt thereof to removal reaction of the carboxy-protective group in $R_a^2$.

Suitable salt of the compounds (I-a) and (I-b) may include the same one as that given for the object compounds (I).

The present reaction is carried out in accordance with a conventional method such as hydrolysis, reduction or the like.

(i) Hydrolysis:

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

The reaction is usually carried out in a solvent such as water, methylene chloride, an alcohol (e.g. methanol, ethanol, etc.), tetrahydrofuran, dioxane or any other solvents which do not adversely influence the reaction, or a mixture thereof. A liquid base or acid can be also used as the solvent.

The reaction temperature is not critical and the reaction is usually carried out under from cooling to warming.

(ii) Reduction:

Reduction can be applied preferably for the removal of the carboxy-protective group such as 4-nitrobenzyl, 2-iodoethyl, 2,2,2-trichloroethyl, or the like. The reduction method applicable for the removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

The reaction is usually carried out in a conventional solvent such as water, alkanol (e.g. methanol, ethanol, propanol, etc.), dioxane, tetrahydrofuran, acetic acid or any other organic solvents which do not adversely influence the reaction, or a mixture thereof.

The reaction temperature is not critical, and the reaction is usually carried out under from cooling to warming.

The present process includes within the scope thereof a case that the protected carboxy group for $R^4$ is transformed into the free carboxy group during the reaction.

(3) Process 3:

The compound (I-d) or a salt thereof can be prepared by subjecting the compound (I-c) or a salt thereof to removal reaction of the carboxy-protective group for $R_a^4$.

Suitable salt of the compounds (I-c) and (I-d) may include the same one as that given for the object compounds (I).

The present reaction is carried out in accordance with a conventional method such as hydrolysis, reduction, or the like as explained in Process 2, and accordingly, the methods of Hydrolysis and Reduction, and the reaction conditions thereof (e.g. reaction reagents, temperature, solvent, etc.) can be referred to those of Process 2.

The present process includes within the scope thereof a case that the protected carboxy moiety in the protected carboxy(lower)alkyl group for $R^2$ is transformed into the free carboxy moiety during the reaction.

The methods for preparing the new starting compounds (III-b) to (III-f) are explained in details in the subsequent Preparations.

It is to be noted that, in the aforementioned reactions in Processes 1 to 3 or the post-treatment of the reaction mixture therein, in case that the starting or object compounds possess an optical and/or geometrical isomer(s), it may occasionally be transformed into the other optical and/or geometrical isomer(s), and such cases are also included within the scope of the present invention.

In case that the object compounds (I) have a free carboxy group for $R^2$ and $R^4$, it may be transformed into its pharmaceutically acceptable salts by a conventional method.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents, especially for oral administration.

Now in order to show the utility of the object compounds (I), the test data on the antimicrobial activity of the representative compound of the object compounds (I) of this invention are shown in the following.

Test Compound: 7-[2-Carboxymethoxyimino-2-(1,2,4-thiadiazol-3-yl)acetamido]-3-cephem-4-carboxylic acid (syn isomer).

Test Method: in vitro Antimicrobial Activities.

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of the test compound, and the minimal inhibitory concentration (MIC) was expressed in terms of μg/ml after incubation at 37° C. for 20 hours.

| Test Results: | |
| --- | --- |
| Test strains | MIC (μg/ml) |
| *Escherichia coli* 31 | 0.05 |
| *Klebsiella pneumoniae* 7 | 0.05 |

For therapeutic administration, the object compounds (I) and the pharmaceutically acceptable salts thereof of the present invention are used in the form of conventional pharmaceutical preparation which contains said compounds, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following examples are given for the purpose of illustrating the present invention.

Preparation of the starting compound (III)

Preparation 1

To a solution of 2-tert-butoxycarbonylmethoxyimino-2-(5-amino-1,2,4-thiadiazol-3-yl)acetic acid (syn isomer (20 g) in ethyl acetate (200 ml) and tetrahydrofuran (100 ml) was added dropwise a solution of diphenyldiazomethane in ethyl acetate (0.9 m mole/ml, 80 ml) at ambient temperature, and the mixture was stirred for an hour. The reaction mixture was washed with a saturated aqueous sodium bicarbonate and an aqueous sodium chloride, and then dried over magnesium sulfate. The solution was evaporated to give benzhydryl 2-tert-butoxycarbonylmethoxyimino-2-(5-amino-1,2,4-thiadiazol-3-yl)acetate (syn isomer) (15.0 g), mp 164° C. (dec.).

IR (Nujol): 3400, 3250, 3100, 1740, 1630, 1530 cm$^{-1}$

NMR (DMSO-d$_6$, δ): 1.48 (9H, s), 4.72 (2H, s), 7.08 (1H, s), 7.36 (10H, m), 8.26 (2H, broad s).

Preparation 2

A solution of t-butyl nitrite (3.2 g) in tetrahydrofuran (20 ml) was added dropwise to a solution of benzhydryl 2-tert-butoxycarbonylmethoxyimino-2-(5-amino-1,2,4-thiadiazol-3-yl)acetate (syn isomer) (10 g) in tetrahydrofuran (100 ml) at 50° to 53° C. under stirring, and the mixture was stirred at the same temperature for 25 minutes. The reaction mixture was poured into a mixture of ethyl acetate and water. The separated organic layer was washed with an aqueous sodium chloride and dried over magnesium sulfate. The solution was evaporated and the residue was subjected to column chromatography on silica gel. The elution was carried out with a mixture of benzene and ethyl acetate (19:1) and the eluates containing the object compound were evaporated to give benzhydryl 2-tert-butoxycarbonylmethoxyimino-2-(1,2,4-thiadiazol-3-yl)acetate (syn isomer) (7.1 g), mp. 139° to 141° C.

IR (Nujol): 1740, 1600, 1490 cm$^{-1}$

NMR (DMSO-d$_6$, δ): 1.42 (9H, s), 4.80 (2H, s), 7.12 (1H, s), 7.38 (10H, m), 10.32 (1H, s).

Preparation 3

To a solution of benzhydryl 2-tert-butoxycarbonylmethoxyimino-2-(1,2,4-thiadiazol-3-yl)acetate (syn isomer) (6.5 g) and anisole (6.5 ml) in methylene chloride (60 ml) was added trifluoroacetic acid (13 ml) at ambient temperature, and the mixture was stirred at the same temperature for 25 minutes. To the reaction mixture was added ethyl acetate and the solution was washed with water. To the separated organic layer was added water and the mixture was adjusted to pH 7.5 with 20% aqueous sodium carbonate. The separated aqueous layer was acidified to pH 2.0 with 10% hydrochloric acid. The acidified solution was saturated with sodium chloride and extracted with ethyl acetate. The ethyl acetate layer was washed with an aqueous sodium chloride, and dried over magnesium sulfate. The solution was evaporated and the residue was pulverized with diisopropyl ether and n-hexane to give 2-tert-butoxycarbonylmethoxyimino-2-(1,2,4-thiadiazol-3-yl)acetic acid (syn isomer) (2.2 g), mp. 137° C. (dec.).

IR (Nujol): 1740, 1600 cm$^{-1}$

NMR (DMSO-d$_6$, δ): 1.46 (9H, s), 4.76 (2H, s), 10.32 (1H, s).

Preparation 4

To a solution of (1,2,5-thiadiazol-3-yl)glyoxylic acid (6 g) in tetrahydrofuran (30 ml) and water (30 ml) was added tert-butoxycarbonylmethoxyamine (8.37 g) at ambient temperature. The mixture was adjusted to pH 4.5–5.0 with 4N aqueous sodium hydroxide and stirred at ambient temperature for 4 hours. The mixture was adjusted to pH 7.5 with 4N aqueous sodium hydroxide and washed with ethyl acetate (100 ml×2). The aqueous solution was acidified to pH 2.0 with 10% hydrochloric acid and extracted with ethyl acetate (100 ml×2). The organic layer was washed with an aqueous sodium chloride and dried over magnesium sulfate. The solution was evaporated in vacuo to give 2-tert-butoxycarbonylmethoxyimino-2-(1,2,5-thiadiazol-3-yl)acetic acid (syn and anti mixture) (10.02 g).

IR (Nujol): 3450, 1720, 1700 cm$^{-1}$.

NMR (DMSO-d$_6$, δ): 1.48 (9H, s), 4.73 (2H, s), 4.82 (2H, s), 8.88 (1H, s), 9.17 (1H, s).

Preparation of the object compounds (I)

Example 1

Vilsmeier reagent was prepared from N,N-dimethylformamide (0.31 g) and phosphorus oxychloride (0.64 g) in a usual manner. 2-tert-butoxycarbonylmethoxyimino-2-(1,2,4-thiadiazol-3-yl)acetic acid (syn isomer) (1.0 g) was added to a stirred suspension of the Vilsmeier reagent prepared above in ethyl acetate (11 ml) under ice-cooling, and the stirring was continued for 30 minutes at the same temperature to produce an activated acid solution. N-Trimethylsilylacetamide (3.2 g) was added to a stirred suspension of 7-amino-3-cephem-4-carboxylic acid (0.7 g) in ethyl acetate (20 ml), and the stirring was continued at 40° to 43° C. for 30 minutes. To this solution was added the above activated acid solution at −10° C., followed by stirring at the same temperature for 30 minutes. Water (10 ml) was added to the resultant solution, and the separated organic layer was washed with water, dried over magnesium sulfate and then evaporated to give 7-[2-tert-butoxycarbonylmethoxyimino-2-(1,2,4-thiadiazol-3-yl)acetamido]-3-cephem-4-carboxylic acid (syn isomer) (1.4 g).

IR (Nujol): 3220, 1780, 1680, 1640, 1540 cm$^{-1}$

NMR (DMSO-d$_6$, δ): 1.40 (9H, s), 3.57 (2H, m), 4.67 (2H, s), 5.07 (1H, d, J=5 Hz), 5.87 (1H, dd, J=5 Hz, 8 Hz), 6.43 (1H, m), 9.58 (1H, d, J=8 Hz), 10.25 (1H, s).

Example 2

Vilsmeier reagent was prepared from phosphorus oxychloride (1.7 g) and N,N-dimethylformamide (0.8 g) in ethyl acetate (3.2 ml) in a usual manner. 2-tert-Butoxycarbonylmethoxyimino-2-(1,2,4-thiadiazol-3-yl)acetic acid (syn isomer) (2.7 g) was added to a stirred suspension of the Vilsmeier reagent prepared above in ethyl acetate (30 ml) under ice-cooling, and the stirring was continued for 40 minutes at the same temperature to produce an activated acid solution. Bis(trimethylsilyl)urea (5.8 g) was added to a stirred suspension of p-nitrobenzyl 7-amino-3-chloro-3-cephem-4-carboxylate hydrochloride (3.8 g) in tetrahydrofuran (40 ml), and the mixture was stirred for 20 minutes at 35° to 40° C. To this solution was added the above activated acid solution at −10° C., followed by stirring for 20 minutes at the same temperature. After water and ethyl acetate were added to the reaction mixture, the separated organic layer was washed with a saturated aqueous sodium bicarbonate and aqueous sodium chloride, and then dried over magnesium sulfate. The solution was evaporated to give p-nitrobenzyl 7-[2-tert-butoxycarbonylmethoxyimino-2-(1,2,4-thiadiazol-3-yl)acetamido]-3-chloro-3-cephem-4-carboxylate (syn isomer) (4.97 g).

IR (Nujol): 1770, 1720, 1680, 1630 cm$^{-1}$

NMR (DMSO-d$_6$, δ): 1.43 (9H, s), 3.83 (2H, m), 4.71 (2H, s), 5.25 (1H, d, J=5.0 Hz), 5.41 (2H, s), 5.96 (1H, dd, J=5.0 Hz, 8.0 Hz), 7.64 (2H, d, J=8.0 Hz), 8.20 (2H, d, J=8.0 Hz), 9.74 (1H, d, J=8.0 Hz), 10.28 (1H, s).

Example 3

Benzhydryl 7-[2-tert-butoxycarbonylmethoxyimino-2-(1,2,4-thiadiazol-3-yl)acetamido]-3-vinyl-3-cephem-4-carboxylate (syn isomer) (2.0 g) was obtained by reacting benzhydryl 7-amino-3-vinyl-3-cephem-4-carboxylate hydrochloride (1.5 g) with an activated acid solution, which was prepared from 2-tert-butoxycarbonylmethoxyimino-2-(1,2,4-thiadiazol-3-yl)acetic acid (syn isomer) (1.0 g), N,N-dimethylformamide (0.31 g) and phosphorus oxychloride (0.64 g), according to a similar manner to that of Examples 1 and 2.

IR (Nujol): 3250, 1780, 1720, 1680, 1530 cm$^{-1}$

NMR (DMSO-d$_6$, δ): 1.43 (9H, s), 3.73 (2H, ABq, J=18 Hz), 4.70 (2H, s), 5.25 (1H, d, J=5 Hz), 5.33 (1H, d, J=11 Hz), 5.57 (1H, d, J=18 Hz), 5.95 (1H, dd, J=5 Hz, 8 Hz), 6.72 (1H, dd, J=11 Hz, 18 Hz), 6.90 (1H, s), 7.33 (10H, m), 9.68 (1H, d, J=8 Hz), 10.23 (1H, s).

Example 4

A syn isomer of benzhydryl 7-[2-tert-butoxycarbonylmethoxyimino-2-(1,2,5-thiadiazol-3-yl)acetamido]-3-vinyl-3-cephem-4-carboxylate (3.03 g) and an anti isomer thereof (1.06 g) was separately obtained by reacting benzhydryl 7-amino-3-vinyl-3-cephem-4-carboxylate hydrochloride (4 g) with the activated acid solution, which was prepared from 2-tert-butoxycarbonylmethoxyimino-2-(1,2,5-thiadiazol-3-yl)acetic acid (a mixture of syn and anti isomers) (2.7 g), N,N-dimethylformamide (1.14 g) and phosphorus oxychloride (2.39 g), according to a similar manner to that of Examples 1 and 2. Syn Isomer:

IR (Nujol): 3250, 1770, 1730, 1705, 1665 cm$^{-1}$

NMR (DMSO-d$_6$, δ): 1.45 (9H, s), 3.58–3.86 (2H, m), 4.7 (2H, s), 5.23 (1H, d, J=11 Hz), 5.25 (1H, d, J=5 Hz), 5.58 (1H, d, J=18 Hz), 5.92 (1H, dd, J=8 Hz, 5 Hz), 6.72 (1H, dd, J=18 Hz, 11 Hz), 6.87 (1H, s), 7.13–7.5 (10H, m), 8.97 (1H, s), 9.68 (1H, d, J=8 Hz).

Anti Isomer:

IR (Nujol): 1770, 1730, 1705, 1665 cm$^{-1}$.

NMR (DMSO-d$_6$, δ): 1.48 (9H, s), 3.67–3.98 (2H, m), 4.89 (2H, s), 5.30 (1H, d, J=11 Hz), 5.32 (1H, d, J=5 Hz), 5.65 (1H, d, J=18 Hz), 5.92 (1H, dd, J=8 Hz, 5 Hz), 6.80 (1H, dd, J=18 Hz, 11 Hz), 6.97 (1H, s), 7.2–7.67 (10H, m), 9.33 (1H, s), 9.60 (1H, d, J=8 Hz).

Example 5

7-[2-tert-Butoxycarbonylmethoxyimino-2-(1,2,4-thiadiazol-3-yl)acetamido]-3-chloro-3-cephem-4-carboxylic acid (syn isomer) was obtained by reacting 7-amino-3-chloro-3-cephem-4-carboxylic acid hydrochloride with the activated acid solution, which was prepared from 2-tert-butoxycarbonylmethoxyimino-2-(1,2,4-thiadiazol-3-yl)acetic acid (syn isomer), N,N-dimethylformamide and phosphorus oxychloride, according to a similar manner to that of Examples 1 and 2.

IR (Nujol): 1770, 1670 (broad) cm$^{-1}$

NMR (DMSO-d$_6$, δ): 1.46 (9H, s), 3.82 (2H, q, J=18.0 Hz), 4.73 (2H, s), 5.28 (1H, d, J=5.0 Hz), 5.91 (1H, dd, J=5.0 Hz, 8.0 Hz), 9.73 (1H, d, J=8.0 Hz), 10.30 (1H, s)

Example 6

Trifluoroacetic acid (3.6 ml) was added to a suspension of 7-[2-tert-butoxycarbonylmethoxyimino-2-(1,2,4-thiadiazol-3-yl)acetamido]-3-cephem-4-carboxylic acid (syn isomer) (1.2 g) in anisole (1.2 ml), and the mixture was stirred for 2 hours at ambient temperature. The resultant solution was added dropwise to diisopropyl ether (100 ml) and the precipitates were collected by filtration. The precipitates were added to a mixture of water (50 ml) and ethyl acetate (50 ml) and adjusted to pH 6.5 with 5% aqueous sodium bicarbonate. The separated aqueous layer was adjusted to pH 2.5 with 10% hydrochloric acid and extracted with ethyl acetate. The extract was washed with water, dried over magnesium sulfate and then evaporated to give 7-[2-carboxymethoxyimino-2-(1,2,4-thiadiazol-3-yl)acetamido]-3-cephem-4-carboxylic acid (syn isomer) (0.5 g).

IR (Nujol): 3250, 1750, 1720, 1670, 1540 cm$^{-1}$

NMR (DMSO-d$_6$, δ): 3.58 (2H, m), 4.73 (2H, s), 5.10 (1H, d, J=5 Hz), 5.90 (1H, dd, J=5 Hz, 8 Hz), 6.45 (1H, m), 9.60 (1H, d, J=8 Hz), 10.23 (1H, s).

Example 7

Trifluoroacetic acid (5.2 ml) was added to a suspension of 7-[2-tert-butoxycarbonylmethoxyimino-2-(1,2,4-thiadiazol-3-yl)acetamido]-3-chloro-3-cephem-4-carboxylic acid (syn isomer) (1.3 g) in methylene chloride (2.5 ml) and anisole (1.3 ml) at ambient temperature, and the mixture was stirred for 1.5 hours at the same temperature. To the resultant solution was added a mixture of diisopropyl ether (30 ml) and n-hexane (15 ml), followed by stirring. The precipitates were collected by filtration and added to a mixture of ethyl acetate and water, followed by adjusting to pH 7.5 with 20% aqueous sodium carbonate. The separated aqueous layer was adjusted to pH 1.8 with 10% hydrochloric acid and saturated with sodium chloride. The resultant aqueous soluiton was extracted with a mixed solvent of ethyl acetate and tetrahydrofuran (2:1 by volume). The extract was washed with a saturated aqueous sodium chloride, dried over magnesium sulfate and then evaporated to give 7-[2-carboxymethoxyimino-2-(1,2,4-thiadiazol-3-yl)acetamido]-3-chloro-3-cephem-4-carboxylic acid (syn isomer) (0.8 g).

IR (Nujol): 1775, 1720, 1680 cm$^{-1}$

NMR (DMSO-d$_6$, δ): 3.82 (2H, q, J=19.0 Hz), 4.75 (2H, s), 5.27 (1H, d, J=4.0 Hz), 5.91 (1H, dd, J=4.0 Hz, 8.0 Hz), 9.73 (1H, d, J=8.0 Hz), 10.27 (1H, s).

Example 8 p-Nitrobenzyl 7-[2-tert-butoxycarbonylmethoxyimino-2-(1,2,4-thiadiazol-3-yl)acetamido]-3-chloro-3-cephem-4-carboxylate (syn isomer) (4.9 g) dissolved in a mixed solvent of methanol (30 ml), tetrahydrofuran (30 ml) and acetic acid (1 ml). After adding 10% palladium on carbon (2.5 g) thereto, the mixture was subjected to catalytic reduction at ambient temperature under atmospheric pressure. The catalyst was removed by filtration, and the filtrate was concentrated under reduced pressure. To the residue were added water and ethyl acetate, and the mixture was adjusted to pH 7.5 with 20% aqueous sodium carbonate. The separated aqueous layer was adjusted to pH 2.0 with 10% hydrochloric acid and then extracted with ethyl acetate. The extract was washed with a saturated aqueous sodium chloride and dried over magnesium sulfate. The solvent was removed by evaporation to give 7-[2-tert-butoxycarbonylmethoxyimino-2-(1,2,4-thiadiazol-3-yl)acetamido]-3-chloro-3-cephem-4-carboxylic acid (syn isomer) (1.4 g).

IR (Nujol): 1770, 1670 (broad) cm$^{-1}$

NMR (DMSO-d$_6$, δ): 1.46 (9H, s), 3.82 (2H, q, J=18.0 Hz), 4.73 (2H, s), 5.28 (1H, d, J=5.0 Hz), 5.91 (1H, dd, J=5.0 Hz, 8.0 Hz), 9.73 (1H, d, J=8.0 Hz), 10.30 (1H, s).

EXAMPLE 9

Trifluoroacetic acid (6.75 ml) was added to a solution of benzhydryl 7-[2-tert-butoxycarbonylmethoxyimino-2-(1,2,5-thiadiazol-3-yl)acetamido]-3-vinyl-3-cephem-4-carboxylate (syn isomer) (2.9 g) in methylene chloride (5.8 ml) and anisole (1.9 ml) under ice-cooling, and the mixture was stirred for 4 hours at ambient temperature. The resultant solution was added dropwise to diisopropyl ether (100 ml) and the precipitates were collected by filtration. The precipitates were added to a mixture of water and ethyl acetate and adjusted to pH 7.0 with 10% aqueous sodium hydroxide. The separated aqueous layer was adjusted to pH 2 with 10% hydrochloric acid and extracted with ethyl acetate. The extract was washed with an aqueous sodium chloride and then dried over magnesium sulfate and evaporated in vacuo. The residue was triturated with diisopropyl ether and collected by filtration to give 7-[2-carboxymethoxyimino-2-(1,2,5-thiadiazol-3-yl)acetamido]-3-vinyl-3-cephem-4-carboxylic acid (syn isomer) (0.96 g).

IR (Nujol): 3250, 1760, 1680 cm$^{-1}$

NMR (DMSO-d$_6$, δ): 3.5–4 (2H, m), 4.85 (2H, s), 5.2 (1H, d, J=5 Hz), 5.27 (1H, d, J=11 Hz), 5.55 (1H, d, J=18 Hz), 5.77 (1H, dd, J=8 Hz, 5 Hz), 6.9 (1H, dd, J=18 Hz, 11 Hz), 9.3 (1H, s), 9.53 (1H, d, J=8 Hz).

Example 10

7-[2-Carboxymethoxyimino-2-(1,2,4-thiadiazol-3-yl)acetamido]-3-vinyl-3-cephem-4-carboxylic acid (syn isomer) (1.0 g) was obtained by reacting benzhydryl 7-[2-tert-butoxycarbonylmethoxyimino-2-(1,2,4-thiadiazol-3-yl)acetamido]-3-vinyl-3-cephem-4-carboxylate (syn isomer) (1.8 g) with trifluoroacetic acid (5.4 ml) in the presence of anisole (1.8 ml) according to a similar manner to that of Example 9.

IR (Nujol): 3200, 1770, 1680, 1610, 1540 cm$^{-1}$.

NMR (DMSO-d$_6$, δ): 3.72 (2H, ABq, J=17 Hz), 4.75 (2H, s), 5.22 (1H, d, J=5 Hz), 5.30 (1H, d, J=11 Hz), 5.55 (1H, d, J=18 Hz), 5.83 (1H, dd, J=5 Hz, 8 Hz), 6.92 (1H, dd, J=11 Hz, 18 Hz), 9.67 (1H, d, J=8 Hz), 10.27 (1H, s).

What we claim is:

1. A compound of the formula:

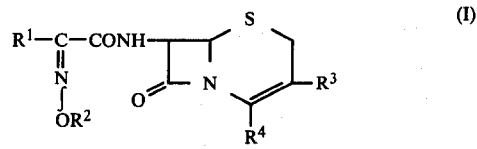

in which
R$^1$ is 1,2,4-thiadiazolyl or 1,2,5-thiadiazolyl,
R$^2$ is carboxy(lower)alkyl or protected carboxy(lower)alkyl,
R$^3$ is hydrogen, halogen or lower alkenyl, and
R$^4$ is carboxy or a protected carboxy group, and pharmaceutically acceptable salts thereof.

2. A compound of claim 1, which is syn isomer.

3. A compound of claim 2, in which R$^1$ is 1,2,4-thiadiazol-3-yl, 1,2,4-thiadiazol-5-yl, or 1,2,5-thiadiazol-3-yl.

4. A compound of claim 3, in which
R$^2$ is carboxy(lower)alkyl or esterified carboxy(lower)alkyl and
R$^4$ is carboxy or esterified carboxy.

5. A compound of claim 4, in which
R$^2$ is carboxy(lower)alkyl and R$^4$ is carboxy.

6. A compound of claim 5, in which R$^1$ us 1,2,4-thiadiazol-3-yl and R$^3$ is hydrogen.

7. A compound of claim 6, which is 7-[2-carboxymethoxyimino-2-(1,2,4-thiadiazol-3-yl)-acetamido]-3-cephem-4-carboxylic acid (syn isomer).

8. A compound of claim 5, in which R$^1$ is 1,2,4-thiadiazol-3-yl and R$^3$ is halogen.

9. A compound of claim 8, which is

7-[2-carboxymethoxyimino-2-(1,2,4-thiadiazol-3-yl)acetamido]-3-chloro-3-cephem-4-carboxylic acid (syn isomer).

10. A compound of claim 5, in which R$^3$ is lower alkenyl.

11. A compound of claim 10, which is 7-[2-carboxymethoxyimino-2-(1,2,4-thiadiazol-3-yl)acetamido]-3-vinyl-3-cephem-4-carboxylic acid (syn isomer) or 7-[2-carboxymethoxyimino-2-(1,2,5-thiadiazol-3-yl)acetamido]-3-vinyl-3-cephem-4-carboxylic acid (syn isomer).

12. A compound of claim 4, in which R$^2$ is esterified carboxy(lower)alkyl and R$^4$ is carboxy.

13. A compound of claim 12, in which R$^2$ is lower alkoxycarbonyl(lower)alkyl.

14. A compound of claim 13, which is 7-[2-tert-butoxycarbonylmethoxyimino-2-(1,2,4-thiadiazol-3-yl)acetamido]-3-cephem-4-carboxylic acid (syn isomer) or 7-[2-tert-butoxycarbonylmethoxyimino-2-(1,2,4-thiadiazol-3-yl)acetamido]-3-chloro-3-cephem-4-carboxylic acid (syn isomer).

15. A compound of claim 4, in which R$^2$ is esterified carboxy(lower)alkyl and R$^4$ is esterified carboxy.

16. A compound of claim 15, in which R$^2$ is lower alkoxycarbonyl(lower)alkyl and R$^4$ is mono- or di- or triphenyl(lower)alkoxycarbonyl which may have nitro.

17. A compound of claim 16, which is p-nitrobenzyl 7-[2-tert-butoxycarbonylmethoxyimino-2-(1,2,4-thiadiazol-3-yl)acetamido]-3-chloro-3-cephem-4-carboxylate (syn isomer), benzhydryl 7-[2-tert-butoxycarbonylmethoxyimino-2-(1,2,4-thiadiazol-3-yl)acetamido]-3-vinyl-3-cephem-4-carboxylate (syn isomer) or benzhydryl 7-[2-tert-butoxycarbonylmethoxyimino-2-(1,2,5-thiadiazol-3-yl)acetamido]-3-vinyl-3-cephem-4-carboxylate (syn isomer).

18. A pharmaceutical composition for treatment of infectious diseases comprising, as active ingredients, a therapeutically effective amount of the compound claimed in claim 1, in admixture with pharmaceutically acceptable carriers.

19. A method for treating infectious diseases caused by pathogenic microorganisms, which comprises administering a therapeutically effective amount of the compound claimed in claim 1 to infected human being or animals.

* * * * *